United States Patent
Campin et al.

(10) Patent No.: US 6,599,286 B2
(45) Date of Patent: Jul. 29, 2003

(54) LASER ABLATION ZONE RESTRICTION SYSTEM AND METHOD

(75) Inventors: John Alfred Campin, Orlando, FL (US); Gary Paul Gray, Orlando, FL (US)

(73) Assignee: Alcon Universal Ltd., Hunenberg (CH)

(*) Notice: Subject to any disclaimer, the term of this patent is extended or adjusted under 35 U.S.C. 154(b) by 168 days.

(21) Appl. No.: 09/842,309

(22) Filed: Apr. 25, 2001

(65) Prior Publication Data

US 2002/0007177 A1 Jan. 17, 2002

Related U.S. Application Data

(60) Provisional application No. 60/199,641, filed on Apr. 25, 2000.

(51) Int. Cl.$^7$ .................... A61N 5/01; A61N 5/067
(52) U.S. Cl. ................ 606/5; 606/10; 607/89
(58) Field of Search ................ 606/5, 10; 607/89

(56) References Cited

U.S. PATENT DOCUMENTS

| | | |
|---|---|---|
| 4,523,821 A | 6/1985 | Lang et al. |
| 4,632,528 A | 12/1986 | Yoshino et al. |
| 4,669,466 A | 6/1987 | L'Esperance |
| 4,688,941 A | 8/1987 | Philbert |
| 4,702,245 A | 10/1987 | Schröder et al. |
| 4,718,418 A | 1/1988 | L'Esperance, Jr. |
| 5,098,426 A | 3/1992 | Sklar et al. |
| 5,214,456 A | 5/1993 | Gersten |
| 5,395,356 A | 3/1995 | King et al. |
| 5,423,801 A | 6/1995 | Marshall et al. |
| 5,442,412 A | 8/1995 | Frey et al. |
| 5,474,548 A | 12/1995 | Knopp et al. |
| 5,505,723 A | 4/1996 | Muller |
| 5,507,741 A | 4/1996 | L'Esperance, Jr. |
| 5,512,965 A | 4/1996 | Snook |
| 5,512,966 A | 4/1996 | Snook |
| 5,556,395 A | 9/1996 | Shimmick et al. |
| 5,592,246 A | 1/1997 | Kuhn et al. |
| 5,632,742 A | 5/1997 | Frey et al. |
| 5,661,773 A | * 8/1997 | Swerdloff et al. ............ 378/65 |
| 5,735,843 A | 4/1998 | Trokel |
| 5,784,146 A | 7/1998 | Nanjo et al. |
| 5,807,381 A | 9/1998 | Lieberman |
| 5,943,117 A | 8/1999 | Van de Velde |
| 5,963,300 A | 10/1999 | Horwitz |
| 6,099,522 A | * 8/2000 | Knopp et al. ................ 606/10 |

FOREIGN PATENT DOCUMENTS

| | | |
|---|---|---|
| DE | 197 52 949 A1 | 6/1998 |
| EP | 0 882 438 A2 | 12/1998 |

* cited by examiner

*Primary Examiner*—Andrew M. Dolinar
(74) *Attorney, Agent, or Firm*—Allen, Dyer, Doppelt, Milbrath & Gilchrist, P.A.

(57) ABSTRACT

A system for protecting a sector of tissue from exposure to surgically directed radiation includes a processor and an input device, a camera, and an output screen in electronic communication with the processor. A software resident on the processor receives camera data containing an image of a region of tissue, which includes at least a portion of a predetermined area desired to receive therapeutic radiation. The software also routes the image for display superimposes thereon first indicia indicative of the predetermined area. Data are received on a location of a sector of the tissue desired to be protected from the radiation and for superimposing on the displayed image second indicia indicative of the sector. In a specific embodiment the tissue is an eye and the predetermined area is at least a portion of the cornea.

47 Claims, 3 Drawing Sheets

LASER ABLATION ZONE RESTRICTION SYSTEM AND METHOD

CROSS-REFERENCE TO RELATED APPLICATION

This application claims priority from commonly owned provisional application Ser. No. 60/199,641, filed Apr. 25, 2000, "Use of Graphical User Interface for Protection of LASIK Flap and Hinge during LASIK Surgery."

BACKGROUND OF THE INVENTION

1. Field of the Invention

The present invention relates to systems and methods for correction visual aberrations, and, more particularly, to such systems and methods for defining a region to be restricted from ablation.

2. Description of Related Art

Laser-in-situ-keratomileusis (LASIK) is a common type of laser vision correction method. It has proven to be an extremely effective outpatient procedure for a wide range of vision correction prescriptions. The use of an excimer laser allows for a high degree of precision and predictability in shaping the cornea of the eye. Prior to the LASIK procedure, measurements of the eye are made to determine the amount of corneal material to be removed from various locations on the corneal surface so that the excimer laser can be calibrated and guided for providing the corrective procedure previously determined by the measurements. Prior to the procedure, a microkeratome is typically used to make a thin, shallow incision in the cornea from the side, top, or bottom to create a hinged flap. During surgery the hinged flap is opened, the flap is positioned on or outside the hinge, and the excimer laser is then used to ablate corneal tissue commensurate with the predetermined corrective procedure.

Ablation is typically carried out discretely at each (x,y) coordinate along the cornea by a laser beam delivery and eye tracking system such as described in U.S. Pat. Nos. 5,980,513; 5,849,006; and 5,632,742, and application Ser. No. 09/566,668, all of which are commonly owned with the present invention, and the disclosures of which are herein incorporated by reference.

Preferably the size of the flap is sufficient for performing the ablation substantially without risk of ablating the hinge or flap. In prior art methods the surgeon could elect to allow the flap/hinge to be ablated, which is not to be desired, or to attempt to cover the flap/hinge, such as with a surgical instrument or partial contact lens, which may result in unwanted ablated material being deposited into the corneal bed.

In addition, a surgeon may desire to protect a region of the cornea from ablation for other reasons, which will be detailed in the following. Further, it would be desirable to protect other areas of the eye from ablation exposure.

SUMMARY OF THE INVENTION

It is therefore an object of the present invention to provide a system and method for protecting a selected region of an eye from exposure to an ablating laser.

It is a further object to provide such a system and method for protecting a hinge and flap created by a microkeratome.

It is another object to provide such a system and method that are software-driven.

It is an additional object to provide such a system and method that function through a graphical user interface.

These and other objects are achieved by the present invention, one embodiment of which comprises a system for protecting a sector of tissue from exposure to surgically directed radiation. The system comprises a processor and input means, a camera, and an output screen in electronic communication with the processor.

A software package resident on the processor has means for receiving camera data containing an image of a region of tissue. The tissue region includes at least a portion of a predetermined area desired to receive therapeutic radiation. The software package also has means for routing the image for display on the screen and means for superimposing on the displayed image first indicia indicative of the predetermined area. Means are also included for receiving via the input means data on a location of a sector of the tissue desired to be protected from the radiation and for superimposing on the displayed image second indicia indicative of the sector.

In a specific embodiment of the system the tissue comprises an eye and the predetermined area comprises at least a portion of the cornea. This is not intended as a limitation, however, and alternate tissue sites, such as internal organs, skin could also be irradiated using the graphical user interface of the system.

The method of the present invention, which is for protecting a sector of tissue from exposure to surgically directed radiation, comprises the step of receiving an image of a region of tissue and displaying the image. First indicia are superimposed on the displayed image, the first indicia indicative of the predetermined area. Data are received on a location of a sector of the tissue desired to be protected from the radiation, and second indicia are superimposed on the displayed image, the second indicia indicative of the sector.

In a preferred embodiment the method is employed on an eye, as for the system discussed above.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
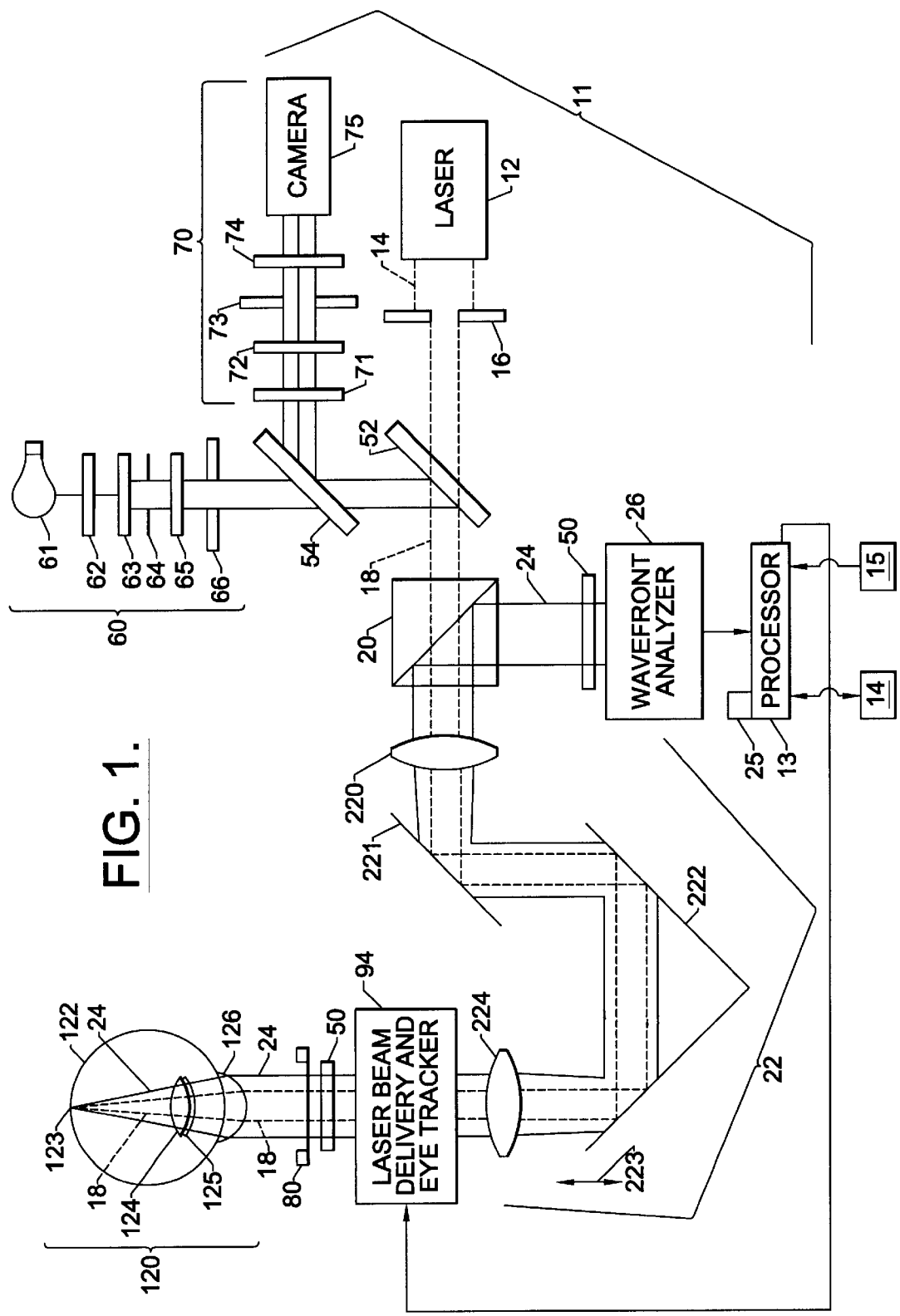
FIG. 1 is a schematic diagram of the system of the present invention.
Figure 2:
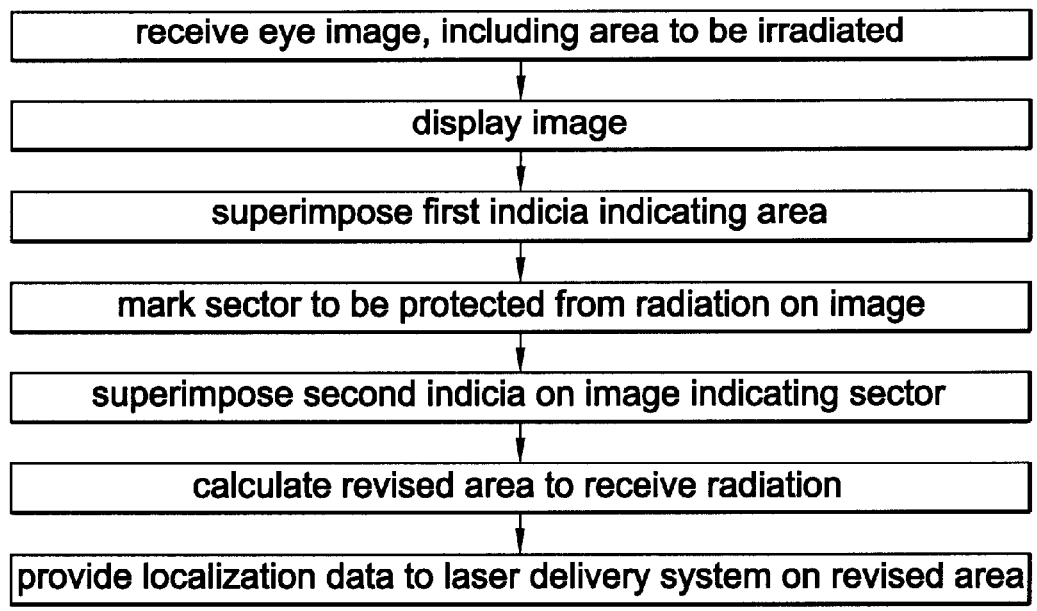
FIG. 2 is a logic flow diagram for the data flow.
Figure 3:
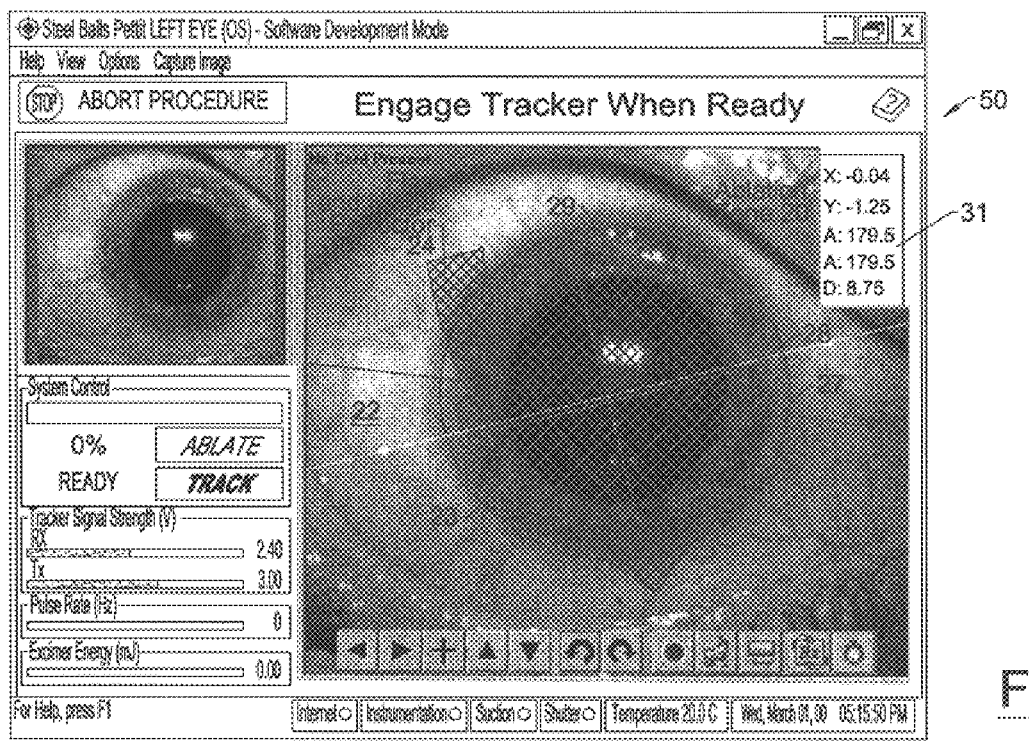
FIG. 3 illustrates an exemplary graphical user interface of the present invention.

A description of the preferred embodiments of the present invention will now be presented with reference to FIGS. 1–3.

An exemplary layout of the system 10 for performing optical measurements and a corrective procedure is illustrated in FIG. 1. This layout is not intended as a limitation, and alternate systems adapted to achieve laser ablation may also be envisioned by one of skill in the art. The eye tracker and laser beam delivery unit 94 comprises a processor 13 in electronic communication with a graphical display 14 having means for receiving input from an operator, such as by means of an input device such as a mouse 15 in electronic communication with the processor 13.

Under various conditions, which will described in the following, a portion of the eye may be desired to be "screened" from the ablation beam. In the example of a graphical user interface 50 illustrated in FIG. 3, an ablation zone 20 is indicated by a cross-hatched area. In a preferred embodiment, the graphical user interface 50 shown would be in color to provide improved contrast against the eye, and the ablation zone 20 would comprise a color that would stand out against the eye, such as yellow.

The flap and hinge in this illustration will have been made along the lower left-hand quadrant of the eye 22, a portion 23 of which resides within the ablation zone 20. In order to protect this portion 23, a protected sector 24 is defined using the mouse 15 and input into a software package 25 resident on the processor 13, which creates the protected sector 24. The protected sector 24 on a color screen 14 would also be a contrasting color, such as blue. The software package 25 then prevents the protected sector 24 from the impinging ablation beam by inhibiting the excimer laser from firing in this sector 24. If the flap is sufficiently large that the flap and hinge do not intersect the ablation zone 20, this definition of a protected sector 24 would not be required.

In a preferred embodiment of the invention, configuration parameters allow for an additional sector adjacent the protected sector 24 to be protected also in order to compensate for the finite extent of the laser pulses. Without this additional sector, a laser shot fired just outside the protected sector 24 may still ablate, to some degree, an area just within the protected sector 24. Similarly, an extracorneal region, such as a conjunctiva or sclera, can be protected from unwanted exposure by, for example, a large, decentered treatment at least a portion of the shots of which could otherwise have extended beyond the cornea.

The graphical user interface 50 of FIG. 3 also has a reticle 26 including a generally circular portion 27 overlying the edge of the cornea 28 and a cross-hair 29, the intersection point 30 positioned generally at a central point of the cornea 28. Data 31 are also provided giving dimensional and positional information.

In addition to protecting the flap and hinge region of the eye, it may also be contemplated to use the present invention in the following:

Avoidance of reexposure of a pre-existing treated zone of tissue, such as might occur during a retreatment for decentration Avoidance of reexposure of tissue during a reoperation to complete an aborted treatment Avoidance of laser exposure of scarred tissue or thin areas where such an exposure would lead to undesired clinical consequences Definition and creation of multiple zones of treatment, such as may be desired to create a multifocal cornea for amelioration of presbyopia Definition and creation of a multifocal cornea by ablation of nearsighted treatment in the midperiphery and a central zone of distance correction Definition and creation of a multifocal cornea by ablation of alternating annuli of distance and near corrections, starting with distance correction in the center of the cornea Definition and creation of a multifocal cornea by ablation of a central distance zone, a midperipheral zone of middle-distance correction (typically ~3 ft), and an outer zone of near correction In addition, one of skill in the art will recognize that the systems and methods of the present invention are amenable for use with other radiative treatments, such as localized irradiation of a tumor, lithotrypsy, removal of a skin disfigurement, or cauterization.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A system for inhibiting surgically directed radiation comprising:
   a processor;
   input means, a camera, and an output screen, all in electronic communication with the processor;
   a software package resident on the processor, the software package capable of:
   (a) receiving camera data containing an image of a region of tissue, the tissue region including at least a portion of a predetermined area desired to receive therapeutic radiation;
   (b) routing the image for display on the screen;
   (c) superimposing on the displayed image first indicia indicative of the predetermined area;
   (d) receiving via the input means data on a location of a sector of tissue desired to be protected from the radiation; and
   (e) superimposing on the displayed image second indicia indicative of the sector of tissue desired to be protected from the radiation.

2. The system recited in claim 1, wherein the software package further is capable of calculating a revised area desired to receive radiation, the revised area comprising the predetermined area minus an intersection area of the predetermined area with the sector of tissue desired to be protected from the radiation.

3. The system recited in claim 2, wherein the processor further has resident thereon a second software package capable of interfacing with and directing a localization of a radiation emitter.

4. The system recited in claim 3, wherein the software package further is capable of interfacing with the second software package for providing localization data on the revised area.

5. The system recited in claim 1, wherein the first and the second indicia comprise a textured graphic.

6. The system recited in claim 1, wherein the first and the second indicia comprise distinct colors selected for providing contrast with the tissue.

7. The system recited in claim 1, wherein the software package further is capable of superimposing on the displayed image third indicia for defining a center of the predetermined area.

8. The system recited in claim 7, wherein the third indicia comprises a cross-hair, an intersection point of which comprises the predetermined area center.

9. The system recited in claim 1, wherein the software package further is capable of displaying relative coordinates of the predetermined area on the screen.

10. The system recited in claim 1, wherein the input means is capable of displaying a pointer on the screen and for tracing an area on the screen representative of the sector using the pointer.

11. The system recited in claim 10, wherein the input means comprises a pointing device.

12. The system recited in claim 10, wherein the screen comprises a touch screen and the input means comprises the touch screen.

13. A system for inhibiting surgically directed laser ablation radiation from impinging on a sector of an eye, the system comprising:
 a processor;
 input means, a camera, and an output screen, all in electronic communication with the processor;
 a software package resident on the processor, the software package capable of:
  receiving camera data containing an image of a region of an eye, the eye region including at least a portion of a predetermined area of a cornea of the eye desired to receive laser ablation radiation;
  routing the image for display on the screen;
  superimposing on the displayed image first indicia indicative of the predetermined area;
  receiving via the input means data on a location of a sector of the eye desired to be protected from the radiation; and
  superimposing on the displayed image second indicia indicative of the sector.

14. The system recited in claim 13, wherein the software package further is capable of calculating a revised area desired to receive radiation, the revised area comprising the predetermined area minus an intersection area of the predetermined area with the sector.

15. The system recited in claim 14, wherein the sector comprises a flap and hinge sector, the flap and hinge having been created prior to ablating the cornea.

16. The system recited in claim 15, wherein the software package further is capable of interfacing with the second software package for providing localization data on the revised area.

17. The system recited in claim 14, wherein the sector comprises at least one of an extracorneal region, a portion of the cornea having been treated in a previous procedure, and a portion of the cornea that is scarred or thin.

18. The system recited in claim 14, wherein the predetermined area comprises a first subarea of the cornea and the sector comprises a second subarea of the cornea distinct from the first subarea.

19. The system recited in claim 14, wherein the processor further has resident thereon a second software package having means for interfacing with and directing a localization of a laser beam delivery system.

20. The system recited in claim 13, wherein the first and the second indicia comprise a textured graphic.

21. The system recited in claim 13, wherein the first and the second indicia comprise distinct colors selected for providing contrast with the eye.

22. The system recited in claim 13, wherein the software package further is capable of superimposing on the displayed image third indicia for defining a center of the predetermined area.

23. The system recited in claim 22, wherein the third indicia comprises a generally circular reticle and a cross-hair, the reticle positionable in surrounding relation to the cornea and an intersection point of the cross-hair comprising the predetermined area center.

24. The system recited in claim 13, wherein the software package further is capable of displaying relative coordinates of the predetermined area on the screen.

25. The system recited in claim 13, wherein the input means is capable of displaying a pointer on the screen and tracing with the pointer an area on the screen representative of the sector.

26. The system recited in claim 25, wherein the input means comprises a pointing device.

27. The system recited in claim 25, wherein the screen comprises a touch screen and the input means comprises the touch screen.

28. A method for inhibiting surgically directed radiation comprising the steps of:
 receiving an image of a region of tissue, the tissue region including at least a portion of a predetermined area desired to receive therapeutic radiation;
 displaying the image;
 superimposing on the displayed image first indicia indicative of the predetermined area;
 receiving data on a location of a sector of the tissue desired to be protected from the radiation;
 superimposing on the displayed image second indicia indicative of the sector; and
 calculating a revised area desired to receive radiation, the revised area comprising the predetermined area minus an intersection area of the predetermined area with the sector.

29. The method recited in claim 28, further comprising the step of directing a localization of a radiation emitter based upon localization data on the revised area.

30. The method recited in claim 28, wherein the first and the second indicia comprise a textured graphic.

31. The method recited in claim 28, wherein the first and the second indicia comprise distinct colors selected for providing contrast with the tissue.

32. The method recited in claim 28, further comprising the step of superimposing on the displayed image third indicia for defining a center of the predetermined area.

33. The method recited in claim 32, wherein the third indicia comprises a cross-hair, an intersection point of which comprises the predetermined area center.

34. The method recited in claim 28, further comprising the step of displaying relative coordinates of the predetermined area on the screen.

35. The method recited in claim 28, further comprising the step of displaying a pointer on the screen and tracing with the pointer an area on the screen representative of the sector.

36. A method for inhibiting surgically directed laser ablation radiation from impinging on a sector of an eye, the method comprising the steps of:
 receiving an image of a region of an eye, the eye region including at least a portion of a predetermined area of a cornea of the eye desired to receive laser ablation radiation;
 displaying the image;
 superimposing on the displayed image first indicia indicative of the predetermined area;
 receiving data on a location of a sector of the eye desired to be protected from the radiation; and
 superimposing on the displayed image second indicia indicative of the sector.

37. The method recited in claim 36, further comprising the step of calculating a revised area desired to receive radiation, the revised area comprising the predetermined area minus an intersection area of the predetermined area with the sector.

38. The system recited in claim 37, wherein the software package further has means for interfacing with a second software package in controlling relation to a radiation emitter for providing localization data on the revised area.

39. The method recited in claim 36, wherein the sector comprises a flap and hinge sector, the flap and hinge having been created prior to ablating the cornea.

40. The method recited in claim 36, wherein the sector comprises at least one of an extracorneal region, a portion of the cornea having been treated in a previous procedure, and a portion of the cornea that is scarred or thin.

41. The method recited in claim 36, wherein the predetermined area comprises a first subarea of the cornea and the sector comprises a second subarea of the cornea distinct from the first subarea.

42. The method recited in claim 36, wherein the first and the second indicia comprise a textured graphic.

43. The method recited in claim 36, wherein the first and the second indicia comprise distinct colors selected for providing contrast with the eye.

44. The method recited in claim 36, further comprising the step of superimposing on the displayed image third indicia for defining a center of the predetermined area.

45. The method recited in claim 44, wherein the third indicia comprises a generally circular reticle and a cross-hair, the reticle positionable in surrounding relation to the cornea and an intersection point of the cross-hair comprising the predetermined area center.

46. The method recited in claim 36, further comprising displaying relative coordinates of the predetermined area on the screen.

47. The method recited in claim 36, further comprising displaying a pointer on the screen and tracing with the pointer an area on the screen representative of the sector.

* * * * *